US012172025B2

(12) United States Patent
Casanova et al.

(10) Patent No.: US 12,172,025 B2
(45) Date of Patent: Dec. 24, 2024

(54) TRANSCRANIAL MAGNETIC STIMULATION FOR THE TREATMENT OF DYSAUTONOMIA

(71) Applicant: UNIVERSITY OF SOUTH CAROLINA, Columbia, SC (US)

(72) Inventors: Manuel Casanova, Simpsonville, SC (US); Emily Casanova, Simpsonville, SC (US); Estate Sokhadze, Greenville, SC (US)

(73) Assignee: UNIVERSITY OF SOUTH CAROLINA, Columbia, SC (US)

( * ) Notice: Subject to any disclaimer, the term of this patent is extended or adjusted under 35 U.S.C. 154(b) by 0 days.

(21) Appl. No.: 16/857,640

(22) Filed: Apr. 24, 2020

(65) Prior Publication Data

US 2020/0406050 A1 Dec. 31, 2020

Related U.S. Application Data

(60) Provisional application No. 62/866,827, filed on Jun. 26, 2019.

(51) Int. Cl.
*A61N 2/00* (2006.01)
*A61N 2/02* (2006.01)

(52) U.S. Cl.
CPC .............. *A61N 2/006* (2013.01); *A61N 2/02* (2013.01)

(58) Field of Classification Search
None
See application file for complete search history.

(56) References Cited

U.S. PATENT DOCUMENTS

| 4,197,851 | A | 4/1980 | Fellus |
| 8,267,851 | B1 | 9/2012 | Kroll |
| 8,579,793 | B1 | 11/2013 | Honeycutt et al. |
| 10,449,384 | B2 * | 10/2019 | Williams ............... A61B 5/165 |

(Continued)

OTHER PUBLICATIONS

Cho, Sang Soo et al., "Continuous theta burst stimulation of right dorsolateral prefrontal cortex induces changes in impulsivity level" 2010, Brain Stimulation, vol. 3, pp. 170-176 (Year: 2010).*

(Continued)

*Primary Examiner* — Christine H Matthews
(74) *Attorney, Agent, or Firm* — DORITY & MANNING, P.A.

(57) ABSTRACT

A method of treating dysautonomia in a human via transcranial magnetic stimulation is provided. The method includes positioning an induction device in proximity to a head region adjacent a prefrontal cortical brain region of the human and delivering magnetic stimulation to the prefrontal cortical region of the human by applying current to the induction device at a frequency that promotes inhibition (e.g., a frequency of about 5 Hertz or less, or certain types of theta bursts). The transcranial magnetic stimulation can introduce variability and/or have a modulatory or a disinhibitory effect on an autonomic nervous system of the human. For instance, the transcranial magnetic stimulation can increase a level of heart rate variability in the human by having a positive modulatory effect on the autonomic nervous system in which autonomic balance is achieved or restored as a result of the stimulation.

18 Claims, 8 Drawing Sheets

(56) References Cited

U.S. PATENT DOCUMENTS

| | | | |
|---|---|---|---|
| 2010/0036191 A1* | 2/2010 | Walter | A61N 2/006 600/14 |
| 2010/0113959 A1* | 5/2010 | Pascual-Leone | A61N 2/008 600/544 |
| 2012/0053449 A1* | 3/2012 | Moses | A61N 1/36025 600/411 |
| 2013/0131537 A1 | 5/2013 | Tam | |
| 2014/0343349 A1* | 11/2014 | Borsody | A61N 2/006 607/17 |
| 2016/0008620 A1* | 1/2016 | Stubbeman | A61B 5/4848 607/45 |
| 2018/0008827 A1* | 1/2018 | Dolev | A61B 5/4824 |

OTHER PUBLICATIONS

Casanova, et al. "Autism spectrum disorders: linking neuropathological findings to treatment with transcranial magnetic stimulation" *Acta Paed.* 104 (2015) pp. 346-355.

Devlin, et al. "Stimulating language: insights from TMS" *Brain* 130 (2007) pp. 610-622.

Fernandez, et al. "Mapping of the human visual cortex using image-guided transcranial magnetic stimulation" *Brain Res. Prot.* 10 (2002) pp. 115-124.

Floel, et al. "Contribution of noninvasive cortical stimulation to the study of memory functions" *Brain Res. Rev.* 53 (2007) pp. 250-259.

Grafman, et al. "Transcranial magnetic stimulation can measure and modulate learning and memory" *Neuropsychologia* 37 (1999) pp. 159-167.

Komissarow, et al. "Triple stimulation technique (TST) in amyotrophic lateral sclerosis" *Clin. Neurophys.* 115 (2004) pp. 356-360.

Lisanby, et al."Applications of TMS to Therapy in Psychiatry" *J. Clin. Neurophys.* 19 (2002) pp. 344-360.

Magstim. "Magstim® Transcranial Magnetic Stimulator" *The Magstim Co. Ltd.* (2010) pp. 1-8.

Oura Crew. What Is Heart Rate Variability and What Can You Learn from It? *Oura* (2017) pp. 1-6.

Ruff, et al. "Combining TMS and fMRI: From 'virtual lesions' to functional-network accounts of cognition" Cortex 45 (2009) pp. 1043-1049.

Rushworth, et al. "Complementary localization and lateralization of orienting and motor attention" *Nat. Neuro.* 4 (2001) pp. 656-661.

Sokhadze, et al. "Ch. 9—Autonomic Nervous System Dysfunctions in Children With Autism Spectrum Disorder" *Autism Spectrum Disorder: Neuromodulation, Neurofeedback and Sensory Integration Approaches to Research and Treatment* (2019) pp. 1-37.

Sokhadze, et al. "Transcranial Magnetic Stimulation in Autism Spectrum Disorders" *Transcranial Magnetic Stimulation: Methods, Clinical Use and Effects on Brain* (2013) pp. 219-231.

Talelli, et al. "Exploring Theta Burst Stimulation as an intervention to improve motor recovery in chronic stroke" *Clin. Neurophys.* 118 (2007) pp. 333-342.

Taylor, et al. "Combining TMS and EEG to study cognitive function and cortico-cortico interactions" *Behav. Brain Res.* 191 (2008) pp. 141-147.

Walsh, et al. "Transcranial magnetic stimulation and cognitive neuroscience" *Nat. Rev Neurosci.* 1 (2000) pp. 73-79.

Wilkinson, et al. "The Contribution of Primary Motor Cortex is Essential for Probabilistic Implicit Sequence Learning: Evidence from Theta Burst Magnetic Stimulation" *J. Cogn. Neurosci.* 22 (2009) pp. 427-436.

Beck, R.C. "Preliminary research report ELF magnetic fields and EEG entrainment" *ELF Infest. Spaces* (1978) pp. 1-7.

Bell, et al. "Alterations in brain electrical activity caused by magnetic fields: Detecting the detection process" *Electroenph. Clin. Neurophys.* 83 (1992) pp. 389-397.

BVE. "Brainwave PhotoStim Deluxe 2.0" *Brainwave Mind Voyages* (1999) pp. 1-5.

Deepak Chopra™ "Dream Weaver" (2012) pp. 1-2. https://www.deepakchopradreamweaver.com/.

Elixa. "Light & Sound Brain Wave Entrainment" *Elixa, Ltd.* (2011) p. 1.

Fields, R.D. "Mind Control by Cell Phone" *Sci. Am.* 7 (2008) pp. 1-3.

König, H.L. "Unsichtbare Umwelt (Invisible Environment)" *Herbert L. König* (1977) pp. 1-209.

Kramarenko, et al. "Effects of high-frequency electromagnetic fields on human Eeg: A brain mapping study" *Int'l J. Neurosci.* 113 (2003) pp. 1007-1019.

Persinger, et al. "Differential entrainment of electroencephalographic activity by weak complex electromagnetic fields" *Percept. Motor Skills* 84 (1997) pp. 527-536.

Pugh, P. "What is the amperage of the electric current running through neurons?" *MadSci Network* (2000) pp. 1-2.

Raz, A. "Could certain frequencies of electromagnetic waves or radiation interfere with brain function?" *Sci. Am.* 29 (2006) pp. 82-83.

Rensberger, B. "Jell-O test finds lifelike signal" *The NY Times* (1976) p. C6.

Schlegel, et al. "50 Years of Schumann Resonance" *Physik in unserer Zeit (Physics in Our Time)* 33 (2002) pp. 256-326.

UCLA. "Hyperactivity in brain may explain multiple symptoms of depression" *UCLA Newsroom* (2012) pp. 1-3.

Von Klitzing, L. "A new encephalomagnetic effect in human brain generated by static magnetic fields" *Brain Res.* 540 (1991) pp. 295-296.

Wikipedia. "Brainwave entrainment" Wikipedia (2015) pp. 1-3.

* cited by examiner

TRANSCRANIAL MAGNETIC STIMULATION FOR THE TREATMENT OF DYSAUTONOMIA

RELATED APPLICATIONS

The present application claims priority to U.S. Provisional Application Ser. No. 62/866,827, filed on Jun. 26, 2019, which is incorporated herein in its entirety by reference thereto.

BACKGROUND OF THE INVENTION

The autonomic nervous system is a control system that unconsciously regulates certain bodily functions, such as heart rate, respiration, digestion, etc. Some individuals, such as those suffering from Autism Spectrum Disorder (ASD), Parkinson's disease, other degenerative neurological diseases, or epilepsy, have an autonomic nervous system that does not function properly to regulate internal temperature, breathing, blood pressure, heart rate, etc. and are thus diagnosed with dysautonomia. Dysautonomia is a condition that affects over 70 million people worldwide in which the autonomic nervous system does not have the ability to adjust in response to various conditions, situations, or the environment. For instance, many individuals with ASD have low heart rate variability (HRV) due to dysautonomia, such that the autonomic nervous system is unable to increase or decrease the heart rate as needed. This condition can lead to early cardiac death for individuals diagnosed with ASD, where the instance of sudden death exceeds that of the normal population by two- to three-fold.

Current treatments for dysautonomia include elevating the head, a high salt diet, and/or the prescribing of drugs, such as fludrocortisone and midodrine. However, these treatments do not cure dysautonomia and treat the symptoms rather than the root cause of the dysautonomia. As such, a need exists for a method of treatment that can normalize such autonomic nervous system dysfunction.

SUMMARY OF THE INVENTION

According to one particular embodiment of the present invention, a method of treating dysautonomia in a human via transcranial magnetic stimulation is provided. The method includes positioning an induction device in proximity to a head region adjacent a prefrontal cortical brain region of the human, and delivering magnetic stimulation to the prefrontal cortical region by applying current to the induction device at a frequency of about 5 Hertz or less or via inhibitory theta bursts at a frequency of about 40 Hertz to about 60 Hertz, wherein the inhibitory theta bursts are delivered as single trains of transcranial magnetic stimulation lasting from about 20 seconds to about 60 seconds.

In one particular embodiment, the transcranial magnetic stimulation can be delivered non-invasively.

In another embodiment, the magnetic stimulation can be delivered to a dorsolateral prefrontal cortex region.

In still another embodiment, the induction device can be free from direct contact with the head region of the human.

In yet another embodiment, the induction device can include a first magnetic coil. Further, the first coil can have a width ranging from about 40 millimeters to about 200 millimeters.

In an additional embodiment, the induction device can include a second magnetic coil. Further, the first coil and the second coil can each have a width ranging from about 40 millimeters to about 100 millimeters.

In one particular embodiment, the magnetic stimulation that is delivered can have a magnetic field strength ranging from about 0.5 Tesla to about 2 Tesla.

In one more embodiment, the method can include measuring one or more physiological parameters of the human during delivery of the magnetic stimulation, after delivery of the magnetic stimulation, or both.

In another embodiment, the magnetic stimulation can be delivered to the human during an initial course of one or more treatment sessions. For instance, the initial course of treatment sessions can include from about 6 treatment sessions to about 30 treatment sessions. Further, in the initial course, the magnetic stimulation can be delivered to the human for a time period ranging from about 15 minutes to about 2 hours per treatment session.

In still another embodiment, a time period between individual treatment sessions in the initial course can range from about 6 hours to about 1 month.

In yet another embodiment, the magnetic stimulation can be delivered to the human during a booster course of one or more treatment sessions after the initial course of one or more treatment sessions is completed. In addition, the magnetic stimulation can be delivered to the human for a time period ranging from about 15 minutes to about 2 hours per treatment session in the booster course.

In one more embodiment, a time period between completion of the initial course and initiation of the booster course can range from about 1 month to about 1 year.

In an additional embodiment, a time period between individual treatment sessions in the booster course can range from about 1 month to about 1 year.

In another particular embodiment, the transcranial magnetic stimulation can normalize a balance of sympathetic and parasympathetic activities in an autonomic nervous system of the human.

In still another embodiment, the transcranial magnetic stimulation can introduce or restore heart rate variability in the human.

Other features and aspects of the present invention are set forth in greater detail below.

Figure 1:
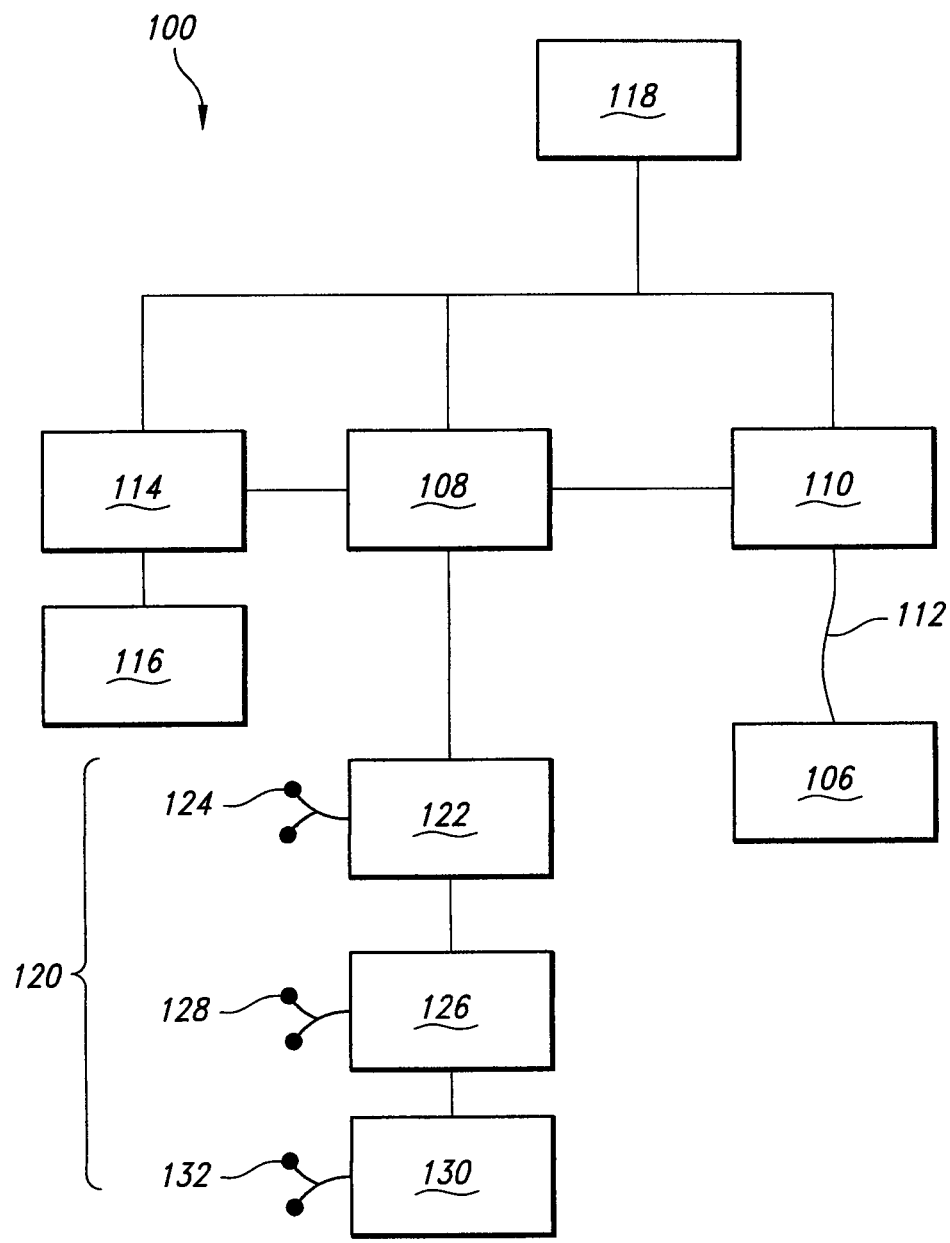
FIG. 1 illustrates one embodiment of a system for treating dysautonomia via transcranial magnetic stimulation according to one embodiment of the present invention.

Repeat use of reference characters in the present specification and drawings is intended to represent the same or analogous features or elements of the present invention.

DETAILED DESCRIPTION

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

As used herein, the terms "about," "approximately," or "generally," when used to modify a value, indicate that the value can be raised or lowered by 5% and remain within the disclosed embodiment. Furthermore, for the purposes of this description, the term "adjacent" is used to describe a situation in which an object is near, in proximity to, or in the vicinity of another object but may not be in direct contact with the other object.

Generally speaking, the present invention is directed to a method of treating dysautonomia in a human via transcranial magnetic stimulation. The method includes positioning an induction device in proximity to a head region adjacent a prefrontal cortical brain region of the human, and delivering magnetic stimulation to the prefrontal cortical region of the human by applying current to the induction device at a frequency of about 5 Hertz or less, or in such a way as to procreate an inhibitory tone in the cerebral cortex. Surprisingly, the present inventors have found that application of the transcranial magnetic stimulation at such a low frequency, which is known by those of ordinary skill in the art as being associated with inhibition, can help normalize autonomic dysfunction in a human. For instance, the transcranial magnetic stimulation can increase a level of heart rate variability in the human by having a modulating effect on the autonomic nervous system.

The autonomic nervous system plays a role in almost every aspect of daily life. For instance, the autonomic nervous system acts a control system that regulates, calibrates, or adjusts the physiologic conditions of the body in response to various events within a number of systems, such as the cardiac, respiratory, digestive, endocrine, and vasomotor systems. In patient's suffering from dysautonomia, the sympathetic or parasympathetic components of the autonomic nervous system do not function properly so that regulation and adjustment of many systems in the body is impacted. Resulting symptoms can include an inability to stay upright; dizziness; vertigo; fainting; a fast heartbeat; a slow heartbeat; an irregular heartbeat; lack of heart rate variability; chest pain; low blood pressure; problems with the gastrointestinal system; nausea; disturbances in the visual field; weakness; breathing difficulties; mood swings; anxiety; fatigue and intolerance to exercise; migraines; tremors; disrupted sleep pattern; frequent urination; temperature regulation problems; concentration and memory problems; poor appetite; and overactive senses, especially when exposed to noise and light. Dysautonomia has been a secondary disorder suffered by patients as a secondary disorder or comorbidity who also suffer from Autism Spectrum Disorder (ASD), Parkinson's disease, other degenerative neurological diseases, or epilepsy as a secondary disorder or comorbidity.

With respect to improving the inability or diminished ability to regulate physiologic conditions associated with dysautonomia, the present inventors have surprisingly found that delivering transcranial magnetic stimulation at a low frequency to the prefrontal cortex can improve a body's ability to regulate functions controlled by the autonomic nervous system. The prefrontal cortex, which includes dorsolateral prefrontal cortex, the ventrolateral prefrontal cortex, and the orbitofrontal cortex, has traditionally been understood as the region of the brain associated with executive function (e.g., working memory), reasoning, decision-making, and moderating of social behavior. In particular, it has been found that delivering transcranial magnetic stimulation at a low frequency to the dorsolateral prefrontal cortex introduces in a patient suffering from dysautonomia the ability to regulate heart rate, as evidenced by the existence or restoration of heart rate variability (e.g., the rate at which a heartbeat changes in time) after treatment via the methods contemplated by the present invention. Meanwhile, without treatment, patients suffering from dysautonomia lack heart rate variability, which is a condition associated with sudden cardiac death.

The specific features of the methods contemplated by the present invention and systems for carrying out the method will now be discussed in more detail below.

Turning first to FIG. 1, a system 100 for treating dysautonomia via transcranial magnetic stimulation is shown. The system 100 can include an induction device 106 for delivering magnetic stimulation that can be coupled to a controller 108 via a cable 112. A signal generator 110, a user interface 114, and a display 116 can also be coupled to the controller 108. The controller 108 can instruct the signal generator 110 to deliver current to the induction device 106 a desired frequency level to then initiate the delivery of magnetic stimulation in the form of a magnetic field to a patient being treated, where it is to be understood that any suitable signal generator can be utilized (e.g., a pulse generator, a capacitor bank discharge system, etc.). For instance, the present inventors have found that the delivery of current on the order of from about 1 kiloamps to about 7.5 kiloamps, such as from about 1.5 kiloamps to about 5 kiloamps, about 2 kiloamps to about 4 kiloamps, or any range therebetween via the signal generator 110 can result in the formation of a magnetic field having a strength ranging from about 0.5 Tesla to about 2 Tesla, such as from about 0.75 Tesla to about 1.1.75 Tesla, such as from about 1 Tesla to about 1.5 Tesla, or any range therebetween. In addition, in one embodiment, the frequency at which the current can be applied can be about 5 Hertz or less, such as from about 0.01 Hertz to about 4 Hertz, about 0.1 Hertz to about 3 Hertz, about 0.5 Hertz to about 2 Hertz, or any range of frequencies therebetween (e.g., about 0.75 Hertz to about 1.5 Hertz). In another embodiment, the magnetic stimulation can be delivered in the form of inhibitory theta bursts at a frequency of about 40 Hertz to about 60 Hertz, such as about 45 Hertz to about 55 Hertz, or about 50 Hertz, wherein the inhibitory theta bursts are delivered as single trains of transcranial magnetic stimulation lasting from about 20 seconds to about 60 seconds, such as from about 25 seconds to about 55 seconds, or from about 30 seconds to about 50 seconds. In addition, the inhibitory theta bursts can be spaced apart by a time frame of about 100 milliseconds to about 300 milliseconds, such as about 125 milliseconds to about 275 milliseconds, or as about 150 milliseconds to about 200 milliseconds.

Figure 2A:
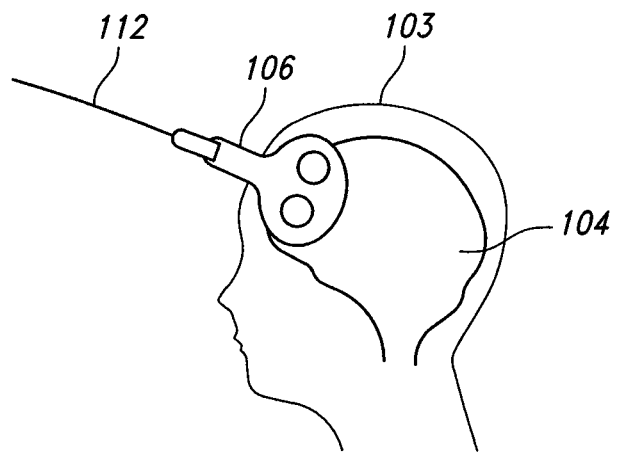
FIG. 2A illustrates the placement of the induction device of the system near a head region of a human according to one embodiment of the present invention.
Figure 2B:
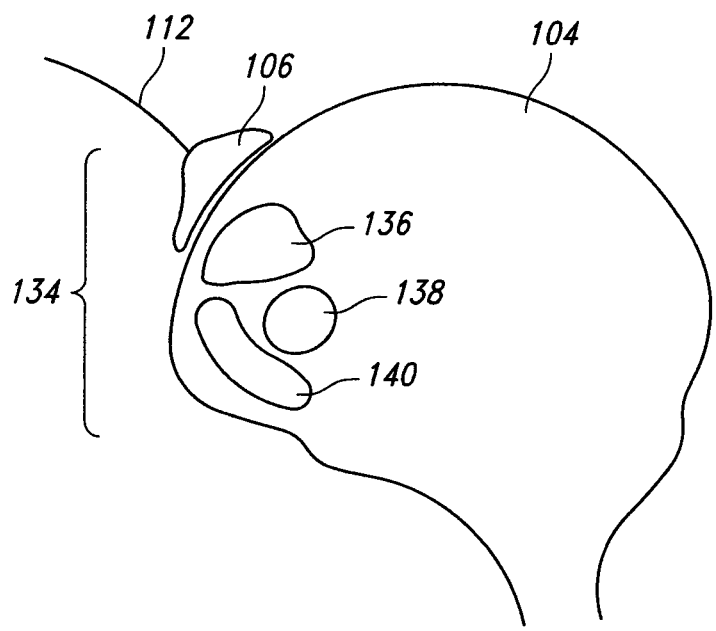
FIG. 2B illustrates the area of the brain stimulated by the placement of the induction device according to FIG. 2A.

Further, the system 100 can include a patient monitor system 120. The patient monitor system 120 can include a heart rate monitor 122 that can include electrocardiogram (ECG) electrodes 124, a skin conductance monitor 126 that can include skin conductance electrodes 128, and any other desired physiologic parameter monitor 132 that can include one or more physiologic parameter electrodes or measuring devices 132. For instance, the physiologic parameter monitor 132 can measure a patient's blood pressure, oxygen levels, respiration rate, temperature, electromyogram (EMG) activity, electroencephalographic (EEG) activity, etc. The entire system 100 can be powered via one or more power supplies 118. The controller 108 can record waveform data and digital information from the patient monitor system 120, such as ECG data, skin conductance data, blood pressure data, oxygen saturation data, respiration data, temperature data, EEG data, EMG data, etc., and can also generate waveform and digital outputs simultaneously for real-time control of the signal generator 130, and thus the delivery of the magnetic stimulation via the induction device 106. The controller 108 can have onboard memory to facilitate high speed data capture, independent waveform sample rates and on-line analysis. Turning now to FIGS. 2A, 2B, 3A, and 3B, the induction device 106 of the system 100 is shown and its placement during treatment is shown. During treatment, the induction device 106 can be positioned near the head region 103 of the patient 102 so as to deliver magnetic stimulation to a desired region of the patient's brain 104, as shown in FIG. 2A. For instance, the induction device 106 can be placed or positioned near the head region of the patent closest to the prefrontal cortical brain region 134, which includes the dorsolateral prefrontal cortex 136, the ventrolateral prefrontal cortex 138, and the orbitofrontal prefrontal cortex 140, as shown in FIG. 2B. Although the induction device 106 is in proximity to the head 104 of the patient 102, the induction device 106 is not in direct contact with the patient 102, and the magnetic stimulation is delivered noninvasively.

Figure 3A:
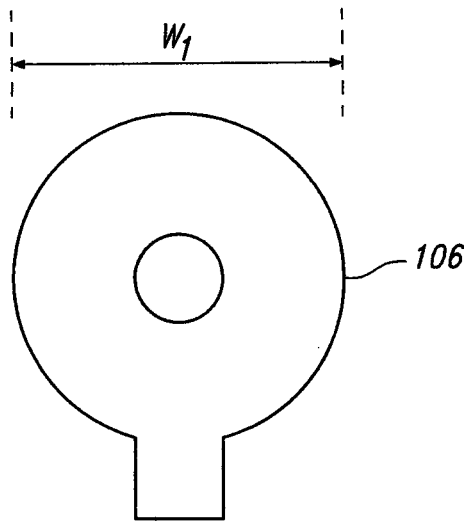
FIG. 3A illustrates one embodiment of a single coil induction device contemplated for use in the system and method for treating dysautonomia contemplated by the present invention.
Figure 3B:
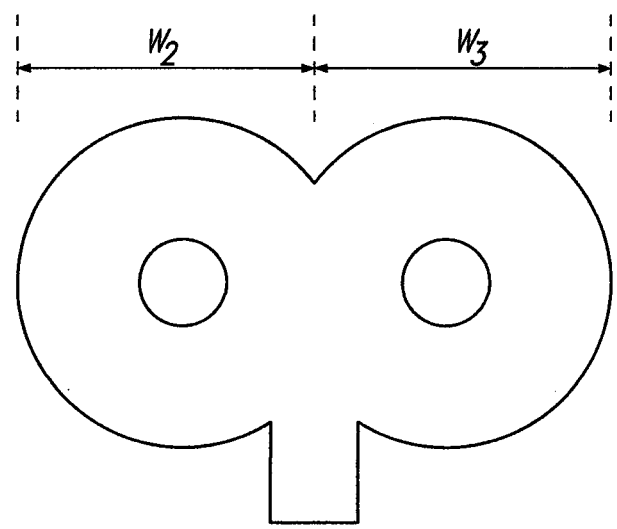
FIG. 3B illustrates another embodiment of a double coil induction device contemplated for use in the system and method for treating dysautonomia contemplated by the present invention.

Turning now to FIGS. 3A and 3B, it is to be understood that any suitable induction device 106 geometry can be used, but, in some embodiments, the induction device 106 can be in the form of a single magnetic coil having a width $W_1$ or a double magnetic coil where the first magnetic coil can have a width $W_2$ and the second magnetic coil can have a width $W_3$. For instance, the width $W_1$ of the single magnetic coil can range from about 40 millimeters to about 200 millimeters, such as from about 50 millimeters to about 180 millimeters, about 60 millimeters to about 160 millimeters, or any range therebetween, while the widths $W_2$ and $W_3$ of the double magnetic coil can each range from about 40 millimeters to about 100 millimeters, such as from about 45 millimeters to about 90 millimeters, about 50 millimeters to about 80 millimeters, or any range therebetween. Further, it is to be understood that in addition to a single coil or double coil, the induction device 106 geometry can be in the form a circle, a figure eight, and H-core, a double cone, etc.

In addition, although the present invention contemplates the delivery of any type or category of transcranial magnetic stimulation (TMS), in one particular embodiment, the method of the present invention contemplates the delivery of repetitive transcranial magnetic stimulation (rTMS) to a patient. In general, during transcranial magnetic stimulation, large magnetic coils are positioned above the patient's head, directly over the desired stimulation area, after which power is supplied to the magnetic coils, causing the magnetic coils to change polarity, which, in turn, produce short magnetic pulses. When these pulses reach the scalp area of the patient's head, they produce an electric current in the nearby neurons located in the brain through a process known as electromagnetic induction. Meanwhile, during rTMS, the speed at which the magnetic coils change polarity is rapidly increased, usually switching between positive and negative polarities in just microseconds. This creates "repetitive" electromagnetic pulses, which create electromagnetic induction having increased strength. Due to the increase in strength, rTMS has the potential to solidify longer lasting changes in the brain, whereby TMS may only induce short-term changes.

Figure 5:
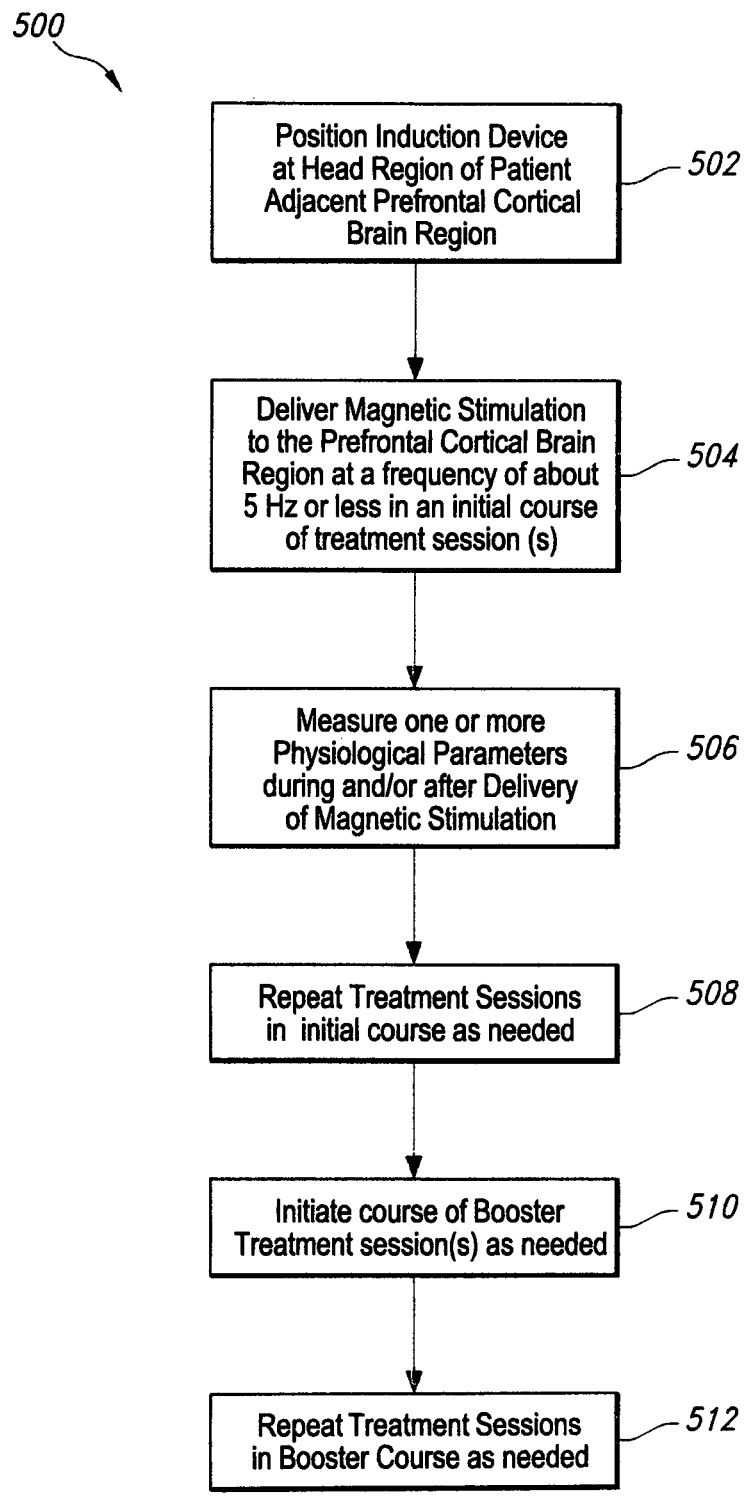
FIG. 5 illustrates a method for treating dysautonomia according to one embodiment of the present invention.

Referring now to FIG. 5, one embodiment of a method of treating dysautonomia according to the present invention is shown. The method 500 includes positioning an induction device at or in proximity of the head region adjacent the prefrontal cortical brain region of a patient in step 502. Then, in step 504, magnetic stimulation is delivered to the prefrontal cortical brain region by applying current at a frequency of about 5 Hz or less to the induction device, such as via the controller. This can be considered an initial course of one or more treatment sessions, where treatment sessions in the initial course can be repeated as needed as shown in step 508, where it is to be understood that one or more of the physiological parameters described above can be measured during and/or after the initial course of one or more treatment sessions, as shown in step 506. Once the desired results are achieved (e.g., improvement in one or more symptoms of dysautonomia), a booster course of one or more treatment sessions can be carried out with a longer duration between the treatment sessions and repeated as needed, as shown in steps 510 and 512.

For instance, the magnetic stimulation can be delivered to the patient during an initial course of treatment sessions that can include from about 6 treatment sessions to about 30 treatment sessions, such as from about 8 treatment sessions to about 25 treatment sessions, about 10 treatment sessions to about 20 treatment sessions, or any range therebetween. Further, the magnetic stimulation can be delivered to the human for a time period ranging from about 15 minutes to about 2 hours per treatment session in the initial course, such as from about 20 minutes to about 1.5 hours per treatment session, about 30 minutes to about 1 hour per treatment session, or any range therebetween. Further, the time period between one treatment session and a subsequent treatment session (e.g., individual treatment sessions) in the initial course can range from about 6 hours to about 1 month, such as from about 12 hours to about 2 weeks, about 24 hours to about 1 week, or any range therebetween.

Additionally, the magnetic stimulation can be delivered to the human during one or more booster courses of one or more treatment sessions. In addition, the magnetic stimulation can be delivered to the human for a time period ranging from about 15 minutes to about 2 hours per treatment session in the booster course, such as from about 20 minutes to about 1.5 hours per treatment session, about 30 minutes to about 1 hour per treatment session, or any range therebetween.

Moreover, the time period between an initial course of one of more treatment sessions and a booster course of one or more treatment sessions (e.g., the time period between a final treatment session in the initial course and a first treatment session in the booster course) can range from about 1 month to about 1 year, such as from about 2 months to about 9 months, about 3 months to about 6 months, or any range therebetween. Further, the time period between one treatment session and a subsequent treatment session (e.g., individual treatment sessions) in the booster course can range from about 1 month to about 1 year, such as from about 2 months to about 9 months, about 3 months to about 6 months, or any range therebetween.

Further, after following the methods described by the present invention, the result of the transcranial magnetic stimulation can be observed in the form of a modulatory effect on the autonomic nervous system of the patient that can normalize the patient's autonomic balance, which is unexpected given the knowledge in the art that low frequency transcranial magnetic stimulation (e.g., less than 2 Hertz) and some types of theta burst stimulation typically have an inhibitory effect (e.g., continuous theta bursts as opposed to intermittent theta bursts, which may be considered to have an excitatory effect), which would lead one to believe that low frequency transcranial magnetic stimulation of the prefrontal cortical region of the brain would inhibit the autonomic nervous system rather than "jumpstart" or initiate a change in the autonomic nervous system of the patient that allows for regulation and adjustment of physiological parameters.

Figure 4A:
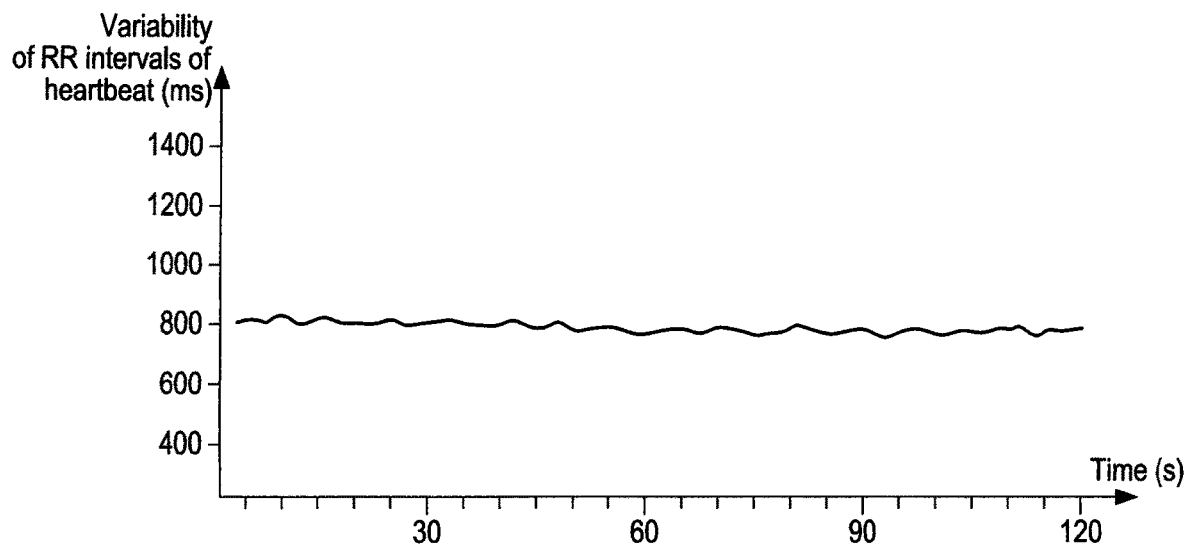
FIG. 4A illustrates a representative graph of the variability of R-R intervals of an ECG versus time for a patient suffering from dysautonomia.
Figure 4B:
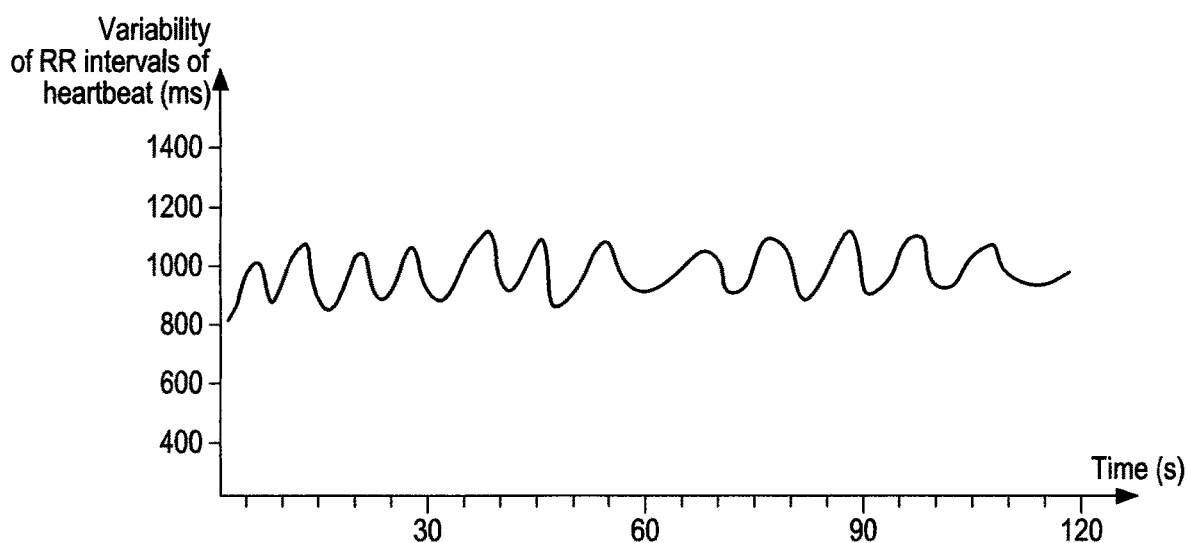
FIG. 4B illustrates a representative graph of the variability of R-R intervals of an ECG versus time for a patient suffering dysautonomia after undergoing an initial course of 18 treatment sessions according to the methods contemplated by the present invention.

For example, and referring to FIGS. 4A and 4B, the transcranial magnetic stimulation contemplated by the system 100 and method 500 of the present invention can restore, introduce, or improve heart rate variability in a patient. FIG. 4A illustrates a representative graph of the variability of R-R intervals of an ECG versus time for a patient suffering from dysautonomia, while FIG. 4B illustrates a representative graph of the variability of R-R intervals of an ECG versus time for a patient suffering dysautonomia after undergoing an initial course of 18 treatment sessions according to the methods contemplated by the present invention. As shown in FIG. 4A, prior to treatment, the patient's R-R interval values are lower and flatter, indicative of a higher heart rate, a lower respiratory sinus arrhythmia, and hence, low heart rate variability over time. For instance, the length of time of the R-R intervals generally stayed constant at about 800 milliseconds over a time period about 2 minutes. This can be a dangerous condition in that the timing of a person's R-R intervals needs to adjust to various factors such as exercise, stress, recovery, etc. On the other hand, after treatment via an initial course of 18 sessions of repetitive transcranial magnetic stimulation according to the methods of the present invention, the patient's heart rate variability was not constant and instead, was variable over a time period of about 2 minutes as shown in FIG. 4B, where the length of time of the patient's R-R-intervals varied between about 800 milliseconds and 1100 milliseconds, where the higher R-R intervals are associated with a lower and more variable heart rate during respiration cycles and high respiratory sinus arrhythmia associated better heart rate variability. This indicates that the patient's autonomic nervous system exhibited restored modulatory function, and as a result, exhibited the ability to regulate the patient's heart rate based on external or internal factors, such as illness, exercise, stress, recovery, etc., after the patient underwent an initial course of 18 treatment sessions according to the methods of the present invention. Essentially, FIG. 4B demonstrates that the methods contemplated by the present invention can normalize autonomic cardiac balance by restoring or improving heart rate variability, which means that after a patient is treated via the methods contemplated by the present invention, the patient exhibits normal respiratory sinus arrhythmia, which assumes variation of a patient's heart rate during the respiration cycle.

The present invention may be better understood with reference to the following example.

Example

Autonomic Activity Measures after 18 Sessions (15-20 Minutes Each) of 0.5 Hertz (Hz) rTMS in 27 Children with ASD (21 Boys and 6 Girls, Mean Age 12.52±2.85 Years) Time-Domain Measures of HRV (R-R Intervals, Standard Deviation of RR [SDNN].

Figure 6:
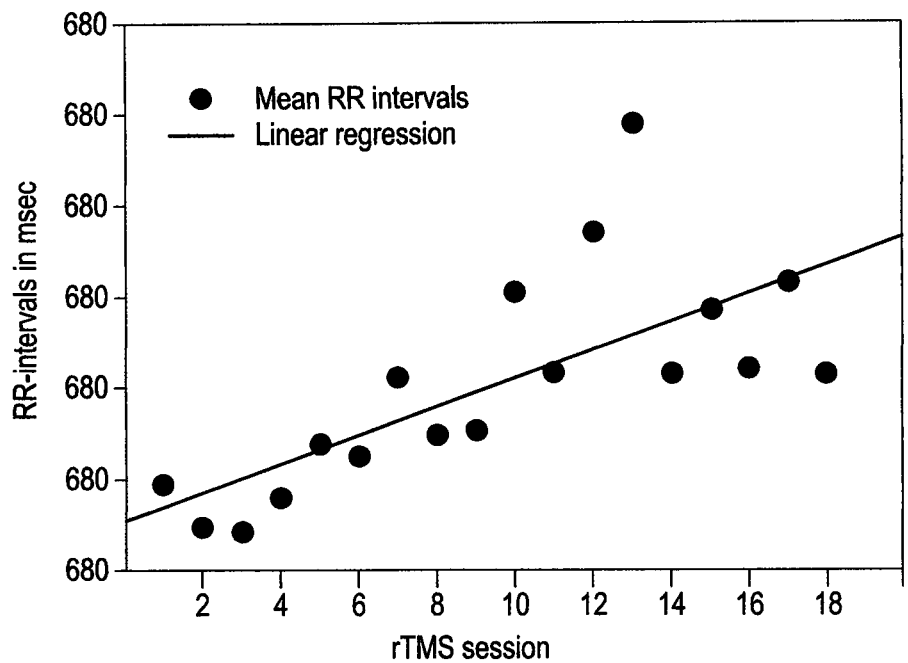
FIG. 6 is a graph illustrating the mean R-R intervals, as well as the linear regression model over 18 sessions of repetitive transcranial magnetic stimulation (rTMS) in children with autism spectrum disorder.
Figure 7:
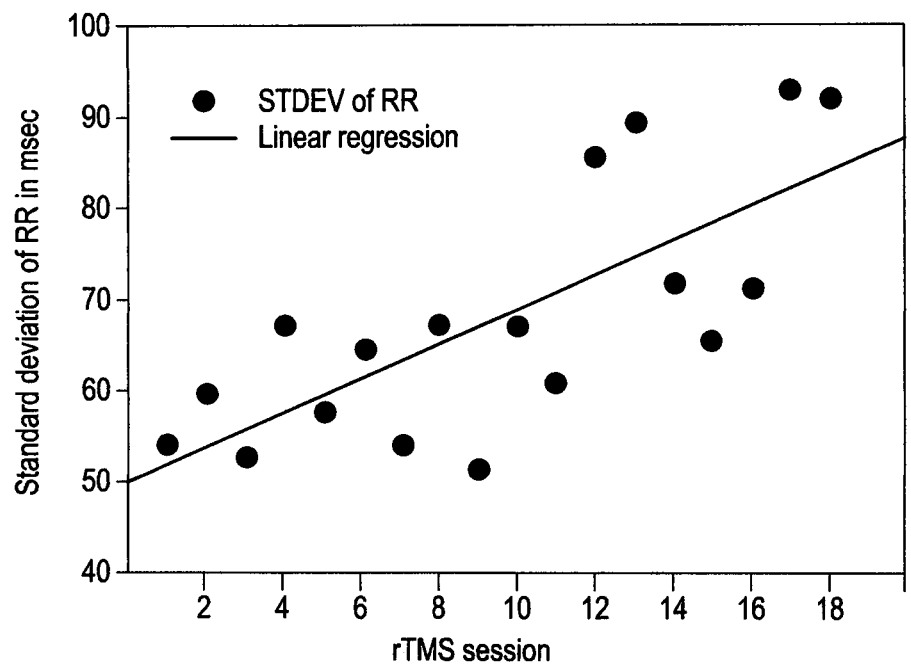
FIG. 7 is a graph illustrating the standard deviation of R-R intervals, as well as the linear regression model over 18 sessions of repetitive transcranial magnetic stimulation (rTMS) in children with autism spectrum disorder.

Cardiointervals in ECG (RR intervals) showed a statistically significant linear regression over 18 sessions of an initial treatment course of rTMS, as shown in FIG. 6. Further, the standard deviation of R-R (SDNN) intervals showed a statistically significant linear increase over the rTMS course of treatment sessions, as shown in FIG. 7. The increased R-R intervals over the course of the 18 treatment sessions of low level 0.5 Hertz rTMS is indicative of increased HRV as evidenced by time-domain measures. Frequency-Domain Measures of HRV (LF and HF of HRV, LF/HF Ratio).

Figure 8:
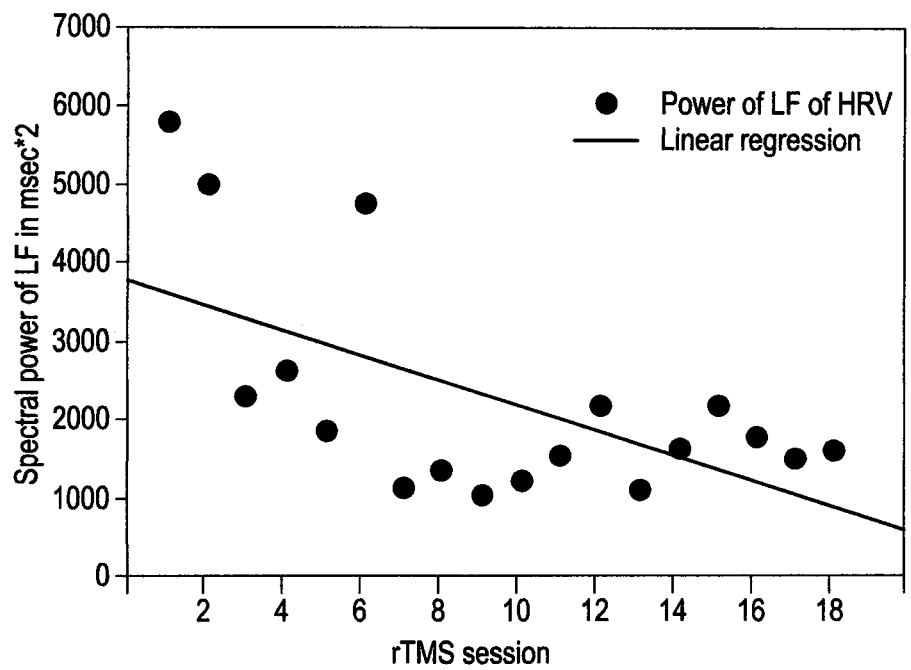
FIG. 8 is a graph illustrating the power of the low frequency component of heart rate variability (HRV), as well as the linear regression model over 18 sessions of repetitive transcranial magnetic stimulation (rTMS) in children with autism spectrum disorder.
Figure 9:
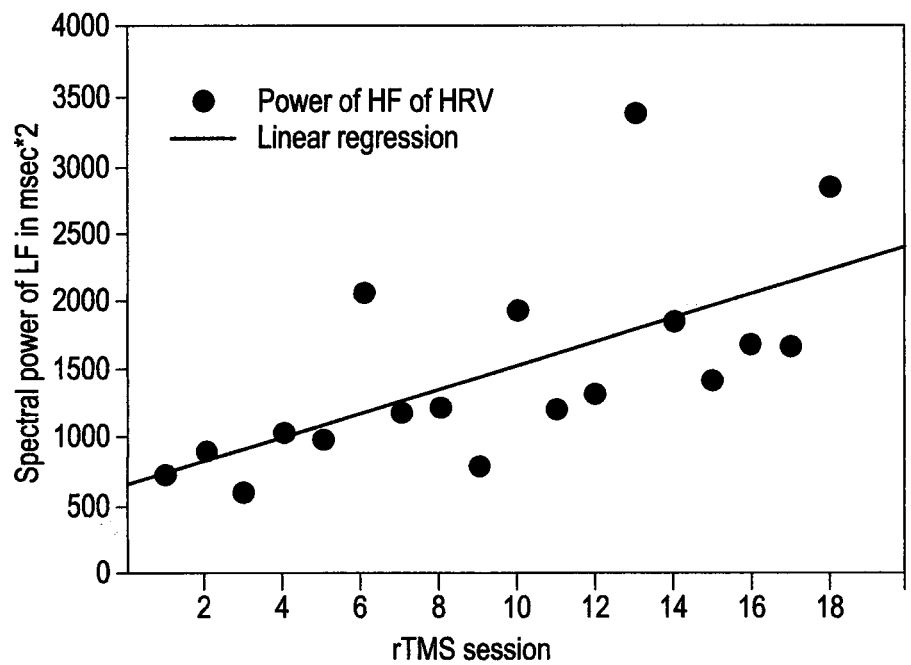
FIG. 9 is a graph illustrating the power of the high frequency component of heart rate variability (HRV), as well as the linear regression model over 18 sessions of repetitive transcranial magnetic stimulation (rTMS) in children with autism spectrum disorder.
Figure 10:
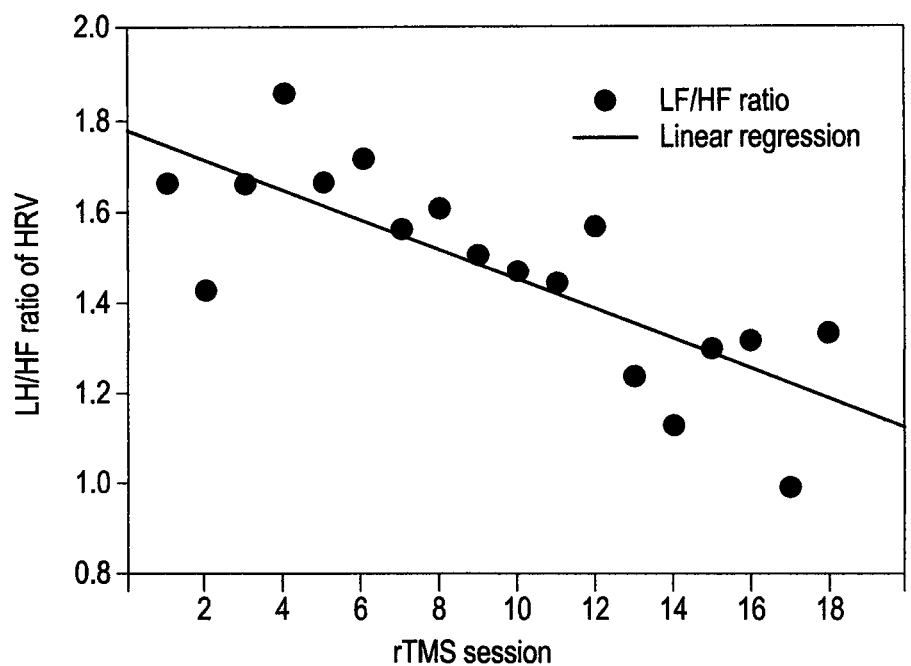
FIG. 10 is a graph illustrating the mean low frequency (LF)/high frequency (HF) ratio of heart rate variability (HRV), as well as the linear regression model over 18 sessions of repetitive transcranial magnetic stimulation (rTMS) in children with autism spectrum disorder.

The power of the Low Frequency (LF) component of HRV—which is predominantly associated with the sympathetic activity index with some parasympathetic contribution—showed a trend towards linear regression, as shown in FIG. 8. The High Frequency (HF) component of HRV—which is associated with the parasympathetic activity index—showed a statistically significant linear increase in power as shown in FIG. 9. Meanwhile, the Low Frequency (LF) component to High Frequency (HF) component ratio showed a decrease over the course of the 18 treatment sessions, as shown in FIG. 10. The decreased LF and LF/HF ratio over the course of the treatment sessions are indicative of decreased sympathetic activation, while increase of HF component of HRV is an indicator of increased parasympathetic activity, these frequency domain measures reflect improved autonomic cardiac balance.

Skin Conductance Level.

Figure 11:
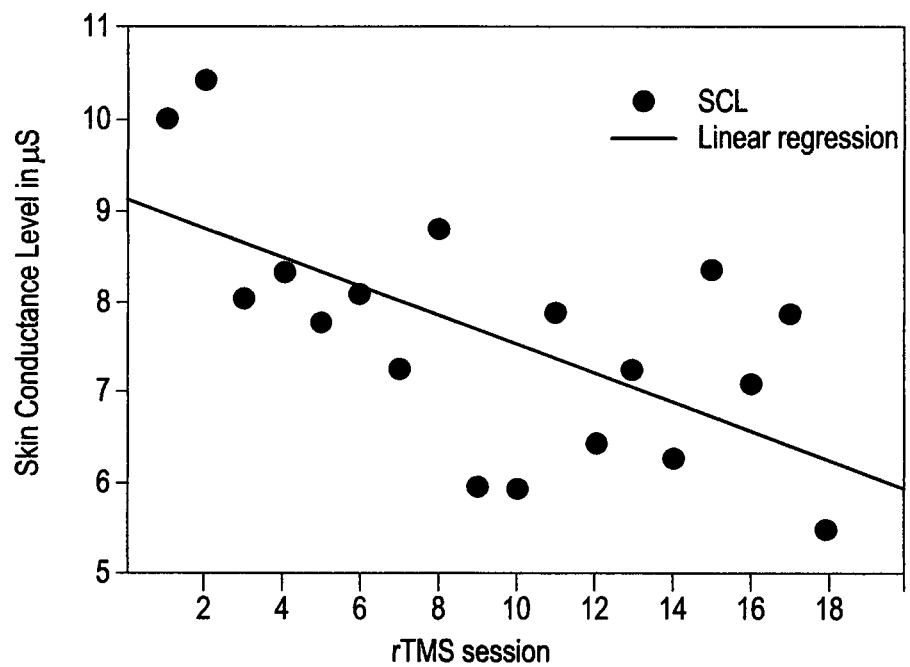
FIG. 11 is a graph illustrating the skin conductance level (SCL), as well as the linear regression model over 18 sessions of repetitive transcranial magnetic stimulation (rTMS) in children with autism spectrum disorder.

Skin conductance level (SCL) testing showed statistically significant linear regression over 18 sessions of rTMS, as shown in FIG. 11. This decrease in skin conductance level is indicative of a decrease of sympathetic activity and modulation or normalization of autonomic arousal.

In summary, as shown above with respect to Study 1 and FIGS. 6-11, time-domain HRV results showed that the most significant changes from TMS treatment were an increase in R-R cardio-interval length and a higher standard deviation of R-R intervals; frequency-domain HRV results showed increase of HF power in HRV, and a decreased LF/HF ratio; electrodermal activity also showed a decrease in the form of lower tonic SCL. The increased standard deviation in cardiointervals, along with higher power of HF of HRV and decreased LF/HF ratio, are promising because this suggests more prominent parasympathetic activity and more flexibility in heart rate overall. Significant change was also observed in mean R-R interval lengths, which means a lower HR. Outcomes within the frequency-domain of HRV showed increased HF component of HRV, which is also of importance as it suggests enhancement of the parasympathetic tone. As there was no observed statistical change in the LF component, it can be inferred that restoration of autonomic balance was achieved mainly through an increased HF component of HRV, which correlates to parasympathetic (vagus) cardiac neural control. However, while the change in the LF component was not significant, a decrease in SCL over the 18 sessions was observed. This result suggests a withdrawal of sympathetic tone as SCL is controlled by sympathetic inputs.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

What is claimed is:

1. A method of treating dysautonomia in a human via transcranial magnetic stimulation, the method comprising:
   positioning an induction device in proximity to a head region of the human adjacent a prefrontal cortical brain region of the human, wherein the induction device is free from direct contact with the head region of the human; and
   delivering magnetic stimulation to the prefrontal cortical region of the human by applying a current to the induction device at a frequency of from about 0.5 Hz to about 3 Hz, wherein the magnetic stimulation to the prefrontal cortical region of the human comprises inhibitory theta bursts at a frequency of about 40 Hertz to about 60 Hertz, wherein the inhibitory theta bursts are delivered as single trains of transcranial magnetic stimulation lasting from 20 seconds to 35 seconds,
   wherein the inhibitory theta bursts are spaced apart by a time frame of about 100 milliseconds to about 150 milliseconds, wherein the magnetic stimulation is delivered to the human for a time period ranging from about 15 minutes to about 2 hours per treatment session in an initial course, and
   wherein the transcranial magnetic stimulation introduces or restores heart rate variability in the human.

2. The method of claim 1, wherein the magnetic stimulation is delivered non-invasively.

3. The method of claim 1, wherein the magnetic stimulation is delivered to a dorsolateral prefrontal cortex region.

4. The method of claim 1, wherein the induction device comprises a first magnetic coil.

5. The method of claim 4, wherein the first coil has a width ranging from about 40 millimeters to about 200 millimeters.

6. The method of claim 4, wherein the induction device comprises a second magnetic coil.

7. The method of claim 6, wherein the first coil and the second coil each have a width ranging from about 40 millimeters to about 100 millimeters.

8. The method of claim 1, wherein the magnetic stimulation has a magnetic field strength ranging from about 0.5 Tesla to about 2 Tesla.

9. The method of claim 1, wherein one or more physiological parameters of the human are measured during delivery of the magnetic stimulation, after delivery of the magnetic stimulation, or both.

10. The method of claim 1, wherein the initial course comprises one or more treatment sessions.

11. The method of claim 10, wherein the initial course includes from about 6 treatment sessions to about 30 treatment sessions.

12. The method of claim 10, wherein a time period between individual treatment sessions in the initial course ranges from about 6 hours to about 1 month.

13. The method of claim 10, wherein the magnetic stimulation is delivered to the human during a booster course of one or more treatment sessions after the initial course of one or more treatment sessions is completed.

14. The method of claim 13, wherein the magnetic stimulation is delivered to the human for a time period ranging from about 15 minutes to about 2 hours per treatment session in the booster course.

15. The method of claim 13, wherein a time period completion of the initial course and initiation of the booster course ranges from about 1 month to about 1 year.

16. The method of claim 13, wherein a time period between individual treatment sessions in the booster course ranges from about 1 month to about 1 year.

17. The method of claim 1, wherein the transcranial magnetic stimulation normalizes a balance of sympathetic and parasympathetic activities in an autonomic nervous system of the human.

18. The method of claim 1, wherein the human has been diagnosed with autism spectrum disorder.

* * * * *